(12) United States Patent
Smith et al.

(10) Patent No.: US 6,982,286 B2
(45) Date of Patent: Jan. 3, 2006

(54) CARBOCYCLIC HYDRAZINO INHIBITORS OF COPPER-CONTAINING AMINE OXIDASES

(75) Inventors: David John Smith, Naantali (FI); Ferenc Fülöp, Szeged (HU); Marjo Pihlavisto, Kaarina (FI); László Lázár, Szeged (HU); Sakari Alaranta, Raisio (FI); Petri Vainio, Turku (FI); Zsolt Szakonyi, Szeged (HU)

(73) Assignee: Biotie Therapies Corp., Turku (FI)

( * ) Notice: Subject to any disclaimer, the term of this patent is extended or adjusted under 35 U.S.C. 154(b) by 224 days.

(21) Appl. No.: 09/902,789

(22) Filed: Jul. 12, 2001

(65) Prior Publication Data

US 2003/0125360 A1 Jul. 3, 2003

(51) Int. Cl.
*A61K 31/135* (2006.01)

(52) U.S. Cl. ............. 514/657; 564/310; 562/590; 562/582; 562/586; 562/584; 562/595; 514/554; 514/574

(58) Field of Classification Search .......... 514/657, 514/554, 574; 564/310; 562/590, 582, 586, 562/584, 595
See application file for complete search history.

(56) References Cited

U.S. PATENT DOCUMENTS 3,105,849 A  10/1963  Huebner ............ 260/501

FOREIGN PATENT DOCUMENTS

| WO | WO 98/55439 | 12/1998 |
| WO | WO 98/55447 | 12/1998 |
| WO | WO 02/02090 A2 | 1/2002 |

OTHER PUBLICATIONS

Chemical Abstract Online, 1992:426035 CAPLUS; Liebigs Annalen der Chemie (1992), (3), 273–8 "Synthesis of amines and amino alcohols by electrophilic amination and highly stereoselective reduction", Gmeiner, Peter; Bollinger, Bernd.*

(Continued)

*Primary Examiner*—Samuel Barts
(74) *Attorney, Agent, or Firm*—Sterne, Kessler, Goldstein & Fox P.L.L.C.

(57) ABSTRACT

The present invention is directed to carbocyclic hydrazino compounds that function as inhibitors of copper-containing amine oxidases commonly known as semicarbazide-sensitive amine oxidases (SSAO), including the human SSAO known as Vascular Adhesion Protein-I (VAP-1). These SSAO inhibitors have therapeutic utility as drugs to treat conditions and diseases including, but not limited to, a number of inflammatory conditions and diseases (in particular chronic inflammatory conditions such as chronic arthritis, inflammatory bowel diseases, and chronic skin dermatoses), diseases related to carbohydrate metabolism and to aberrations in adipocyte differentiation or function and smooth muscle cell function, and vascular diseases. The novel compounds have the general formula:

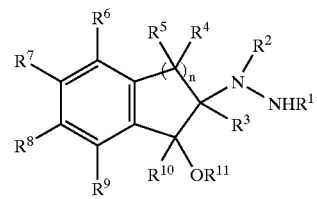

or a pharmaceutically acceptable solvate, hydrate, or salt thereof wherein $R^1$ to $R^{11}$ are as defined herein.

11 Claims, 2 Drawing Sheets

Inhibition of carrageenan-evoked paw oedema in rats by compound 4.
Ctr = vehicle (water), 2027-100 = 4 at a dose of 100 mg kg$^{-1}$ $p < 0.001$

OTHER PUBLICATIONS

Huebner, C.F., et al., "The Azodiformate Adduct of Indene and the Stereochemistry of Some 1,2–Disubstituted Indans," *J. Org. Chem.* 35:1149–1154, American Chemical Society (1970).

Lizcano, J.M., et al., "Inhibition of Bovine Lung Semicarbazide–Sensitive Amine Oxidase (SSAO) by Some Hydrazine Derivatives," *Biochem. Pharmacol.* 52:187–195 (1996).

Arvilommi, A.–M., et al., "Lymphocyte binding to vascular endothelium in inflamed skin revisited: a central role for vascular adhesion protein–1 (VAP–1)," *Eur. J Immunol.* 26:825–833, VCH Verlagsgesellschaft mbH (1996).

CAS Registry No. 13935–78–9, Chemical Abstracts Service (1992).

CAS Registry No. 91182–14–8, Chemical Abstracts Service (No Entry/Publication date available).

CAS Registry No. 91182–13–7, Chemical Abstracts Service (No Entry/Publication date available).

CAS Registry No. 94467–44–4, Chemical Abstracts Service (No Entry/Publication date available).

Huebner, C.F., et al., "Azodiformate adduct of indene and the stereochemistry of some 1,2–disubstituted indans," *Chem. Abstracts* 72:121451t, American Chemical Society (1970).

Lyles, G.A., "Mammalian Plasma and Tissue–bound Semicarbazide–sensitive Amine Oxidases: Biochemical, Pharmacological and Toxicological Aspects," *Int. J. Biochem. Cell Biol.* 28:259–274, Pergamon Press (1996).

Salmi, M. and Jalkanen, S., "A 90–Kilodalton Endothelial Cell Molecule Mediating Lymphocyte Binding in Humans," *Science* 257:1407–1409, American Association for the Advancement of Science (1992).

Salmi, M. and Jalkanen, S., "Human Vascular Adhesion Protein 1 (VAP–1) Is a Unique Sialoglycoprotein that Mediates Carbohydrate–dependent Binding of Lymphocytes to Endothelial Cells," *J. Exp. Med.* 183:569–579, Rockefeller University Press (1996).

Salmi, M., et al., "Induction and Function of Vascular Adhesion Protein–1 at Sites of Inflammation," *J. Exp. Med.* 178:2255–2260, Rockefeller University Press (1993).

Salmi, M., et al., "Homing of Mucosal Leukocytes to Joints. Distinct Endothelial Ligands in Synovium Mediate Leukocyte–subtype Secific Adhesion," *J. Clin. Invest.* 99:2165–2172, American Society for Clinical Investigation (1997).

Salmi, M., et al., "Vascular Adhesion Protein 1 (VAP–1) Mediates Lymphocyte Subtype–specific, Selectin–independent Recognition of Vascular Endothelium in Human Lymph Nodes," *J. Exp. Med.* 186:589–600, Rockefeller University Press (1997).

Salmi, M., et al., "A Cell Surface Amine Oxidase Directly Controls Lymphocyte Migration," *Immunity* 14:265–276, Cell Press (Mar. 2001).

Smith, D.J., et al., "Cloning of Vascular Adhesion Protein 1 Reveals a Novel Multifunctional Adhesion Molecule," *J. Exp. Med.* 188:17–27, Rockefeller University Press (1998).

Urry, W.H., et al., "Electrophilic Addition of 1,1–dimethyldiazenium bromide with 1,3–dienes and styrenes," *Chem. Abstracts* 61:299c, American Chemical Society (1964).

Von Gustarf, K., et al., "Photochemical and thermal 1,2– and 1,4–cycloaddition reactions of azodicarbonyl compounds with monoolefins," *Chem. Abstracts* 72:121454w, American Chemical Society (1970).

\* cited by examiner

Fig. 1 Inhibition of carrageenan-evoked paw oedema in rats by compound 4.
Ctr = vehicle (water), 2027-100 = 4 at a dose of 100 mg kg$^{-1}$ Fig. 2 Inhibition of collagen-induced arthritis in mouse by compound 4. Control= Vehicle (water), 2027-10 = 4 at a dose of 10 mg kg$^{-1}$, 2027-50 = 4 at a dose of 50 mg kg$^{-1}$.

CARBOCYCLIC HYDRAZINO INHIBITORS OF COPPER-CONTAINING AMINE OXIDASES

BACKGROUND OF THE INVENTION

1. Field of the Invention

The present invention is in the field of medicinal chemistry and is directed to carbocyclic hydrazino compounds and their use as inhibitors of copper-containing amine oxidases (E.C. 1.4.3.6) and enzymes of significant identity thereto. The compounds of the present invention have therapeutic utility as drugs to treat diseases including, but not limited to, inflammatory diseases. In particular, acute and chronic inflammatory conditions or diseases such as chronic arthritis, inflammatory bowel diseases and skin dermatoses as well as diseases related to carbohydrate metabolism and to aberrations in adipocyte differentiation or function and smooth muscle cell function may be treated with the compounds.

2. Related Art

VAP-1 is a human endothelial cell adhesion molecule that has several unique properties that distinguish it from the other inflammation-related adhesion molecules. It has a unique and restricted expression pattern and mediates lymphocyte binding to vascular endothelium (Salmi, M., and Jalkanen, S., *Science* 257:1407–1409 (1992)). Inflammation induces the upregulation of VAP-1 to the surface of vascular endothelial cells mediating leukocyte entry to skin, gut and inflamed synovium (Salmi, M., and Jalkanen, S., *Science* 257:1407–1409 (1992); Salmi, M, et al., *J. Exp. Med* 178:2255–2260 (1993); Arvillomi, A., et al., *Eur. J. Immunol* 26:825–833 (1996); Salmi, M., et al., *J. Clin. Invest.* 99:2165–2172 (1997): (Salmi. M., and Jalkanen, S., *J. Exp. Med.* 183:569–579 (1996); *J. Exp. Med* 186:589–600 (1997)). One of the most interesting features of VAP-1 is a catalytic extracellular domain which contains a monoamine oxidase activity (Smith, D. J., et al., *J. Exp. Med* 188:17–27 (1998)).

The cloning and sequencing of the human VAP-1 cDNA revealed that it encodes a transmembrane protein with homology to a class of enzymes called the copper-containing amine oxidases (E.C. 1.4.3.6). Enzyme assays have shown that VAP-1 possesses a monoamine oxidase (MAO) activity which is present in the extracellular domain of the protein (Smith, D. J., et al., *J. Exp. Med.* 188:17–27 (1998)). Thus, VAP-1 is an ecto-enzyme. Anylysis of the VAP-1 MAO activity showed that VAP1 belongs to the class of membrane-bound MAO's termed semicarbazide-sensitive amine oxidases (SSAO). These are distinguished from the widely distributed mitochondrial MAO-A and B flavoproteins by amino acid sequence, cofactor, substrate specificity and sensitivity to certain inhibitors. However, certain substrates and inhibitors are common to both SSAO and MAO activities. The mammalian SSAO's can metabolize various monoamines produced endogenously or absorbed as dietary or xenobiotic substances. They act principally on primary aliphatic or aromatic monoamines such as methylamine or benzylamine (Lyles G. A., *Int. J. Biochem. Cell Biol,* 28:259–274 (1996)). Thus, VAP-1 located on the vascular endothelial cell surface can act on circulating primary monoamines with the following reaction pathway.

$RNH_2 + O_2 + H_2O \rightarrow RCHO + H_2O_2 + NH_3$

The physiological substrates of VAP-1 SSAO in man have not been clearly identified however methylamine is a good substrate for VAP-1 SSAO. Methylamine is a product of various human biochemical pathways for the degradation of creatinine, sarcosine and adrenaline, and is found in various mammalian tissues and in blood. It can also be derived from the diet by gut bacterial degradation of dietary precursors. The concentration of methylamine in the blood can be increased in certain physiological and pathological situations such as diabetes. Another potential physiological substrate is aminoacetone.

VAP-1 SSAO activity has been proposed to be directly involved in the pathway of leukocyte adhesion to endothelial cells by a novel mechanism involving direct interaction with an amine substrate presented on a VAP-1 ligand expressed on the surface of a leukocyte (Salmi et al. *Immunity*, (2001)). This publication describes the direct involvement of VAP-1 SSAO activity in the process of adhesion of leukocytes to endothelium. Thus Inhibitors of VAP-1 SSAO activity could be expected to reduce leukocyte adhesion in areas of inflammation and thereby reduce leukocyte trafficking into the inflamed region and therefore the inflammatory process itself.

In human clinical tissue samples expression of VAP-1 is induced at sites of inflammation. This increased level of VAP-1 can lead to increased production of $H_2O_2$ generated from the action of the VAP-1 SSAO extracellular domain on monoamines present in the blood. This generation of $H_2O_2$ in the localized environment of the endothelial cell could initiate other cellular events. $H_2O_2$ is a known signaling molecule that can upregulate other adhesion molecules and this increased adhesion molecule expression may lead to enhanced leukocyte trafficking into areas in which VAP-1 is expressed. It also may be that other products of the VAP-1 SSAO reaction could have biological effects also contributing to the inflammatory process Thus the products of the VAP1 SSAO activity may be involved in an escalation of the inflammatory process which could be blocked by specific SSAO inhibitors.

VAP-1 SSAO may be involved in a number of other pathological conditions associated with an increased level of circulating amine substrates of VAP-1 SSAO. The oxidative deamination of these substrates would lead to an increase in the level of toxic aldehydes and and oxygen radicals in the local environment of the endothelial cell which could damage the cells leading to vascular damage. Increased levels of methylamine and aminoacetone have been reported in patients with Type I and Type II diabetes and it has been proposed that the vasculopathies such as retinopathy, neuropathy and nephropathy seen in late stage diabetes could be treated with specific inhibitors of SSAO activity.

The development of specific VAP-1 SSAO inhibitors that modulate VAP-1 activity would be useful for the treatment of acute and chronic inflammatory conditions or diseases such as chronic arthritis, inflammatory bowel diseases, and skin dermatoses, as well as diseases related to carbohydrate metabolism (including diabetes and complications resulting from diabetes). In addition, aberrations in adipocyte differentiation or function and smooth muscle cell function (in particular, atherosclerosis), and various vascular diseases may be suitable for treatment with VAP-1 SSAO inhibitors.

SUMMARY OF THE INVENTION

The present invention is broadly directed to novel carbocyclic hydrazino compounds of Formula I as well as the use thereof as inhibitors of the class of copper-containing amine oxidases known as semicarbazide-sensitive amine oxidases (SSAO), including the human SSAO known as Vascular Adhesion Protein-1 (VAP-1). As VAP-1 SSAO inhibitors, compounds of the present invention can function to prevent leukocyte adhesion events mediated through SSAO activity as well as other functions of VAP-1 SSAO. Compounds of the present invention are therefore useful for treating a number of inflammatory conditions and diseases of connective tissue, skin, and the gastrointestinal, central nervous system, and pulmonary systems, including such conditions as chronic arthritis, inflammatory bowel diseases, and chronic dermatoses. The compounds are also useful for treating diseases related to carbohydrate metabolism (such as diabetes), to aberrations in adipocyte differentiation or function or smooth muscle cell function (such as atherosclerosis and obesity), and to various vascular diseases (such as atheromatous and nonatheromatous ateriosclerosis, ischemic heart disease, and peripheral aterial occlusion).

A further aspect of the present invention is to provide a pharmaceutical composition useful for treating disorders responsive to a decrease in SSAO activity, containing an effective amount of a compound of Formula I in a mixture with one or more pharmaceutically acceptable carriers or diluents.

Another embodiment of the present invention is directed to methods for making compounds of Formula I.

One aspect of the present invention is directed to novel compounds of Formula I:

I or an isomer or a pharmaceutically acceptable solvate, hydrate, or salt thereof;
wherein:
$R^1$ is hydrogen or $(C_1-C_4)$alkyl, aralkyl,$(C_2-C_5)$alkanoyl, aroyl or heteroaroyl;
$R^2$ is hydrogen, optionally substituted $(C_1-C_4)$alkyl or optionally substituted aralkyl;
$R^3-R^5$ and $R^{10}$, which can be the same or different, are hydrogen, optionally substituted $(C_1-C_4)$alkyl, optionally substituted aralkyl, optionally substituted phenyl or optionally substituted heteroaryl;
$R^3$ and $R^{10}$ are cis or trans arranged;
$R^{11}$ is hydrogen, $(C_1-C_4)$alkyl, $(C_2-C_5)$alkanoyl or aralkyl;
$R^6-R^9$, which can be the same or different, are hydrogen, optionally substituted $(C_1-C_4)$alkyl, halogen, hydroxy, optionally substituted $(C_1-C_4)$alkoxy, optionally substituted aralkyloxy, or $(C_1-C_4)$alkylamino;
n is 1, 2 or 3, with the proviso that $R^1$ is not methyl when $R^2$ is methyl, n is 1 and $R^3$ to $R^{11}$ are hydrogen.

DETAILED DESCRIPTION OF THE INVENTION

In the description, "$(C_1-C_4)$alkyl" in the meaning of an alkyl group, or as part of an alkoxy, alkanoyl or alkyl amino group can be methyl, ethyl, n-propyl, isopropyl, n-butyl, seo-butyl, tert-butyl and isobutyl.

The term "$(C_2-C_5)$-alkanoyl" as employed herein thus refers to a carbonyl moiety to which is attached an alkyl group, such as any of the above $C_1-C_4$ alkyl groups. For example, this term includes, but is not limited to, ethanoyl, propanoyl, butanoyl, 2-methyl propanoyl.

The term "halogen" or "halo" as employed herein by itself or as part of another group refers to chlorine, bromine, fluorine or iodine, with chlorine being preferred.

The term "substituted", unless otherwise provided for herein, refers to one or more groups independently selected from the group consisting of halo, hydroxy, amino, di($C_1-C_4$)alkylamino, halo($C_1-C_4$) alkyl, ar($C_1-C_4$)alkyl, aryl, nitro, ($C_1-C_4$)alkoxy, and ($C_1-C_4$)alkyl as long, as the resulting compound is stable. Preferred optional substituents include: halo, ($C_1-C_4$)alkyl, hydroxy and ($C_1-C_4$)alkoxy and di($C_1-C_4$)alkyl amino.

Illustrative examples of "substituted ($C_1-C_4$)alkyl group" are trifluoromethyl, 2,2,2-trifluoroethyl, 2,2-dichloroethyl, 2,2,2-trichloroethyl, 2-hydroxyethyl, 3-hydroxyethyl, 3-(dimethylamino)propyl and 2-methoxyethyl.

Aroyl means an aryl group connected to a carbonyl group, Such an aryl can be an monocyclic or bicyclic aromatic group containing from 6 to 12 carbons in the ring portion, preferably 6–10 carbons in the ring portion, such as phenyl, naphthyl or tetrahydronaphthyl. A preferred aryl group is phenyl, which can be substituted or unsubstituted. Preferable substituents are lower alkyl (i.e., $C_1-C_4$ alkyl), especially methyl, or a halogen or lower alkoxy, such as methoxy, or nitro. As particular preferred embodiments can be mentioned benzyl, p-methylbenzyl, p-chlorobenzyl, 2-phenylethyl and 3-phenylpropyl.

The term "aralkyl" as employed herein, or as a part of an aralkyloxy group, should be interpreted as any aryl, such as those mentioned above, attached to the alkyl, which is a chain of 1 to 6 carbon atoms and which in turn can be straight or branched. Preferably, the chain contains 1 to 3 carbon atoms. A preferred aryl group is phenyl, which can be substituted or unsubstituted. Preferable substituents and embodiments are those mentioned above for aryl.

Illustrative examples of "substituted phenyl group" are o-tolyl, m-tolyl, p-tolyl, p-fluorophenyl, p-chlorophenyl.

The term "heteroaryl" as employed herein or as a part of heteroaroyl, refers to groups having 5 to 14 ring atoms and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazoyly, chromenyl, xanthenyl, phenoxathilnyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl phenanthridinyl, acridinyl, perimidinyl, phenanthrolinyl, phenazinyl, isothiazolyl, phenothiazinyl, isoxazolyl, furazanyl and phenoxazinyl groups).

Illustrative and preferred "heteroaryl groups" are 2-pyridyl, 3-pyridyl, 4-pyridyl, 2-furyl, 3-furyl, 1-thienyl, 2-thienyl.

According to a preferred embodiment, in the compound of the Formula I, n has the meaning of 1.

According to a further embodiment, in the compound of Formula I, $R^1$ has the meaning of hydrogen.

According to another preferred embodiment, in the compound of the Formula I, R² has the meaning of unsubstituted allyl, such as methyl.

According to another preferred embodiment, in the compound of the Formula I, R¹¹ is hydrogen.

According to another preferred embodiment, in the compound of the Formula I, R³ is hydrogen.

According to a further preferred embodiment, in the compound of the Formula I, R⁴, R⁵ and R¹⁰ are hydrogen.

According to still a further preferred embodiment, in the compound of the Formula I, R⁶, R⁷, R⁸ and R⁹ are hydrogen.

According to a second aspect, the invention is directed to a method for the preparation of the compounds of Formula I.

Compounds I were synthesized starting from amino alcohols II either via N-nitroso derivatives III or via oxadaizines IV. Nitroso compounds III were obtained from amino alcohols II in slightly acidic aqueous solution by using sodium nitrite (A. A. Potekhin, A. O. Safronov, *Zhur. Org. Khim.*, 1981, 17, 379–386; H. Takahashi, T. Senda, K. Higashiyama, *Chem. Pharm. Bull.*, 1991, 39, 836–842; J-K. Shen, H. Katayama, N. Takatsu, I. Shiro, *J. Chem. Soc. Perkin Trans. I*, 1993, 2087–2097) or by using other well known methods of N-nitrosation (M. A. Zolfigol, M. H. Zebarjadian, G. Chehardoli, H. Keypour, S. Salehzadeh, M. Shamsipur, *J. Org. Chem.*, 2000, 66, 3619–3620). Reductions of nitroso compounds III were done either in tetrahydrofurane by using lithium aluminium hydride (H. Takahashi, T. Senda, K. Higashiyama, *Chem. Pharm. Bull.*, 1991, 39, 836–842) or in aqueous acetic acid by using zinc dust (D. L. Trepanier, V. Sprancmanis, K. G. Wiggs, *J. Org. Chem.*, 1964, 29, 668–672). Acidic hydrolysis of oxadiazines IV (R¹² and R¹³ are (C₁–C₄)alkyl groups or can together represent a 5–7-membered saturated carbocycle), obtained from amino alcohols II and oxaziridines V (E. Schmitz, S. Schramm, Cs. Szántay, Zs. Kardos, *Liebigs Ann. Chem.*, 1993, 1043–1046), yielded hydrazino alcohols I. In the compound I obtained, the groups R¹¹ and R¹ are hydrogen. These groups can be converted to other groups R¹¹ and R¹ e.g. using known methods of alkylation and acylation.

I

II

III

IV

V

Amino alcohols II were used as single diastereomers. The synthesis of the enantiomers of compounds I started from enantiomerically pure amino alcohols II. Transformations occurred without noticeable racemization.

The compounds I of this invention are useful in the form of acid addition salts. The expression "pharmaceutically acceptable acid addition salt" is intended to apply to any non-toxic organic and inorganic acid addition salts of the base compounds of formula I. Illustrative inorganic acids, which form suitable salts include hydrochloric, hydrobromic, sulfuric and phosphoric acids, Illustrative organic acids, which form suitable salts include acetic, lactic, malonic, succinic, glutaric, fumaric, malic, tartaric, citric, ascorbic, maleic, benzoic, phenylacetic, cinnamic, methanesulfonic and salicylic acids.

According to a further aspect, the invention concerns a method of inhibiting a copper-containing amine oxidase, the said method comprising contacting said amine oxidase with an inhibitory effective amount of a compound of the Formula I'

I' or an isomer or a pharmaceutically acceptable solvate, hydrate, or salt thereof;
wherein:
R¹ is hydrogen or (C₁–C₄)alkyl, aralkyl, (C₂–C₅)alkanoyl, aroyl or heteroaroyl;
R² is hydrogen, optionally substituted (C₁–C₄)alkyl, or optionally substituted aralkyl;
R³–R⁵ and R¹⁰, which can be the same or different, are hydrogen, optionally substituted (C₁–C₄)alkyl, optionally substituted aralkyl, optionally substituted phenyl or optionally substituted heteroaryl;
R³ and R¹⁰ are cis or trans arranged;
R¹¹ is hydrogen, (C₁–C₄)alkyl, (C₂–C₅)alkanoyl or aralkyl;

$R^6$–$R^9$, which can be the same or different, are hydrogen, optionally substituted $(C_1-C_4)$alkyl, halogen, hydroxy, optionally substituted $(C_1-C_4)$alkoxy, optionally substituted aralkyloxy, or $(C_1-C_4)$alkylamino;

n is 1,2 or 3.

In one embodiment, the compounds of Formula I are used to treat or prevent connective tissue inflammatory conditions and diseases. In particular, the compounds can be used to treat such conditions or diseases as rheumatoid arthritis, ankylosing spondylitis, psoriatic arthritis, and osteoarthritis.

In another embodiment, the compounds of Formula I are used to treat or prevent gastrointestinal inflammatory conditions and diseases, in particular those such as Crohn's disease, ulcerative colitis, and irritable bowel syndrome.

In yet another embodiment, the compounds of Formula I are used to treat central nervous system inflammatory conditions and diseases, including multiple sclerosis, Alzheimer's disease, and ischaemia-reperfusion injury associated with ischemic stroke.

In another embodiment, the compounds of Formula I are used to treat or prevent pulmonary inflammatory conditions and diseases. In particular, the compounds can be used to treat or prevent such conditions or diseases as asthma and adult respiratory distress syndrome.

In another embodiment, the compounds of Formula I are used to treat or prevent chronic inflammatory skin conditions, especially such inflammatory skin conditions as psoriasis, allergic lesions, lichen planus, and pityriasis rosea.

In yet another embodiment the compounds of Formula I are used to treat or prevent diseases related to carbohydrate metabolism and complications thereof, such as diabetes and complications from diabetes, microvascular and macrovascular diseases such as atherosclerosis, vascular retinopathies, nephropathies and neuropathies such as polyneuropathy, mononeuropathies, and autonomic neuropathy.

In still another embodiment, the compounds of Formula I are used to treat or prevent diseases related to or caused by aberrations in adipocyte differentiation or function, such as atherosclerosis or obesity.

In another embodiment, the compounds of Formula I are used to treat or prevent diseases related to or caused by aberrations in smooth muscle cell function, such as atherosclerosis.

In another embodiment, the compounds of Formula I are used to treat or prevent vascular diseases, such as atheromatous and nonatheromrntous arteriosclerosis, ischemic heart disease, and Raynaud's Disease and Phenomenon, The present invention is also directed to pharmaceutical compositions of these novel compounds of Formula I, as well as to methods of making such compositions.

Some of the compounds disclosed herein may contain one or more asymmetric centers and may thus give rise to enantiomers, diastereomers, and other stereoisomeric forms which are all included in the invention. The present invention is also meant to encompass racemic mixtures, resolved forms and mixtures thereof, as well as the individual enantiomers that may be separated according to methods that are well know to those of ordinary skill in the art. When the compounds described herein contain olefinic double bonds or other centers of geometric asymmetry, and unless specified otherwise, it is intended to include both E and Z geometric isomers.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "asymmetric center" or "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule. The phrase "enantiomeric excess" refers to a mixture wherein one enantiomer is present is a greater concentration than its mirror image molecule.

When any variable occurs more than one time in any constituent or in Formula I, its definition on each occurrence is independent of its definition at every other occurrence. Also, combinations of substituents and/or variables are permissible only if such combinations result in stable compounds.

The present invention provides a method of treating diseases in which VAP-1 has a role by selectively inhibiting VAP-1 SSAO activity, which method comprises administering to an animal in need thereof a therapeutically effective amount of a compound selected from the class of compounds depicted by Formula I, wherein one or more compounds of Formula I is administered in association with one or more non-toxic, pharmaceutically acceptable carriers and/or diluents and/or adjuvants and if desired other active ingredients.

The compounds of the present invention can be used to treat inflammatory conditions and diseases including but not limited to connective tissue inflammatory conditions and diseases such as ankylosing spondylitis, Reiter's syndrome, psoriatic arthritis, osteoarthritis or degenerative joint disease, rheumatoid arthritis, Sjögren's syndrome, Behcet's syndrome, relapsing polychondritis, systemic lupus erythematosus, discoid lupus erythematosus, systemic sclerosis, eosinophilic fasciitis, polymyositis and dermatomyositis, polymyalgia rheumatic; vasculitis, temporal arteritis, polyarteritis nodosa, Wegener's granulomatosis, mixed connective tissue disease, and juvenile rheumatoid arthritis; gastrointestinal inflammatory conditions and diseases such as Crohn's disease, ulcerative colitis, irritable bowel syndrome (spastic colon), fibrotic conditions of the liver, inflammation of the oral mucosa (stomatitis), and recurrent aphtous stomatitis; central nervous system inflammatory conditions and diseases such as multiple sclerosis, Alzheimer's disease, and ischaemia-reperfusion injury associated with ischemic stroke; pulmonary inflammatory conditions and diseases such as asthma, chronic obstructive pulmonary disease, and adult respiratory distress syndrome; and skin inflammatory conditions and diseases such as contact dermatitis, atopic dermatitis, psoriasis, pityriasis rosea, lichen planus, and pityriasis rubra pilaris.

Moreover, the compounds of the invention can be used to treat diseases related to carbohydrate metabolism and complications thereof, such as diabetes and complications of diabetes including, but not limited to microvascular and macrovascular disease such as atherosclerosis, vascular retinopathies, retinopathy, nephropathy and nephrotic syndrome, neuropathies such as polyneuropathy, mononeuropathies, and autonomic neuropathy, and foot ulcers and joint problems, as well as increased risk of infection; diseases related to or caused by aberrations in adipocyte differentiation or function such as atherosclerosis and obesity; and vascular diseases such as atheromatous and nonatheromatous ateriosclerosis, ischemic heart disease including myocardial infarction, peripheral aterial occlusion, thromboangiitis obliterans (Buerger's disease), and Raynaud's disease and phenomenon.

In particular, the present compounds can be used to treat atherosclerosis. It is known that VAP1 is expressed on adipocytes, smooth muscle cells, endothelial cells and is related to inflammation. Atherosclerotic plaque consists of accumulated intracellular and extracellular lipids, smooth muscle cells, connective tissue, and glycosaminoglycans. The earliest detectable lesion of atherosclerosis is the fatty streak (consisting of lipid-laden foam cells, which are macrophages that have migrated as monocytes from the circulation into the subendothelial layer of the intima), which later evolves into the fibrous plaque (consisting of intimal smooth muscle cells surrounded by connective tissue and intracellular and extracellular lipids).

The term "treat inflammation" is intended to include the administration of compounds of the present invention to a subject for purposes, which can include prophylaxis, amelioration, prevention or cure of an inflammatory condition or disease. Such treatment need not necessarily completely ameliorate the inflammatory condition or disease. Further, such treatment can be used in conjunction with other traditional treatments for reducing the inflammatory condition known to those of skill in the art.

The compounds of the present Invention may be administered in an effective amount within the dosage range of about 0.1 $\mu$g/kg to about 300 mg/kg, preferably between 1.0 $\mu$g/kg to 10 mg/kg body weight. Compounds of the present invention may be administered in a single daily dose, or the total daily dosage may be administered in divided doses of two, three or four times daily.

The pharmaceutical compositions of the present invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intraarticular, intrathecal, intramuscular, intraperitoneal, or intradermal injections, or by transdermal, buccal, oromucosal, ocular routes or via inhalation. Alternatively, or concurrently, administration can be by the oral route. Particularly preferred is oral administration. The dosage administered will be dependent upon the age, health, and weight of the recipient, kind of concurrent treatment, if any, frequency of treatment, and the nature of the effect desired.

In addition to the pharmacologically active compounds, the pharmaceutical preparations of the compounds can contain suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Slow-release and prolonged-release formulations may be used with particular excipients such as methacrylic acid-ethylacrylate copolymers, methacrylic acid-ethyl acrylate copolymers, methacrylic acid-methyl methacrylate copolymers and methacrylic acid-methyl methylacrylate copolymers. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Especially preferred salts are maleate, fumarate, succinate, S,S tartrate, R,R tartrate. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

(1S,2S)-2-(1-methylhydrazino)-1-indanol hydrogenmaleate (1)

A solution of NaO$_2$(11.25 g, 163 mmol) in H$_2$O (80 ml) was added dropwise to a suspension of(1S,2S)-2-methylamino- 1-indanol (13.30 g, 81.5 mmol) in H₂O (150 ml) with vigorous stirring on an ice-cold bath, and then AcOH (7.39 g, 123 mmol) was added dropwise. The mixture was stirred at room temperature for 12 h, then was extracted with EtOAc (4×150 ml). The combined organic phases were dried (sicc, Na₂SO₄) and evaporated under reduced pressure to give 14.35 g N-nitroso derivative as a crystalline product which was used in the next step without further purification, A solution of (1S,2S)-2-methylamino-N-nitroso-1-indanol (10.00 g, 52.0 mmol) in THF (80 ml) was added dropwise to a strirred and ice-cooled suspension of LiAlH₄ (3.95 g, 104 mmol) in THF (200 ml), and the mixture was stirred at ambient temperature for 3 h. The excess of LiAlH₄ was decomposed with a mixture of H₂O (8 ml) and THF (50 ml), the resulting precipitate was filtered off and washed with EtOAc (4×100 ml). The combined filtrate and washings were dried (sicc. Na₂SO₄) and evaporated under reduced pressure. The crystalline residue was treated with an equivalent amount of maleic acid in a mixture of EtOH and Et₂O to give crystalline hydrogenmaleate salt which was filtered off and recrystallized.

¹H-NMR (400 MHz, D₂O) δ (ppm); 3.08 (4H, om, CHCH₂, NCH₃), 3.43 (1H, m, CHCH₂), 3.87 (1H, m, NCH), 5.47 (1H, d, J=6.6 Hz, OCH), 6.29 (2H, s, CHCOOH), 7.34 (1H, m, C₆H₄), 7.39 (3H, m, C₆H₄).

EXAMPLE 2
(1R*,2R*)-2-(1-Ethylhydrazino)-1-indanol hydrogenmaleate (2)

A solution of NaNO₂ (1.38 g, 20 mmol) in H₂O (10 ml) was added dropwise to a suspension of (1R*,2R*)-2-ethylamino-1-indanol (1.77 g, 10 mmol) in H₂O (50 ml) with vigorous stirring on an ice-cold bath, and then AcOH (0.90 g, 15 mmol) was added dropwise. The mixture was stirred at room temperature for 8 h, then was extracted with EtOAc (4×50 ml). The combined organic phases were dried (sicc. Na₂SO₄) and evaporated under reduced pressure to give 1.95 g N-nitroso derivative as crystalline product which was used in the next step without further purification.

A solution of (1R*,2R*)-2-ethylamino-N-nitros-1-indanol (1.95 g. 9.5 mmol) in THF (20 ml) was added dropwise to a strirred suspension off LiAlH₄ (0.72 g, 19.0 mmol) in THF (50 ml), and the mixture was stirred and refluxed for 2 h. The excess of LiAlH₄ was decomposed with a mixture of H₂O (1.5 ml) and THE (20 ml), the resulting precipitate was filtered off and washed with EtOAc (2×75 ml). The combined filtrates were dried (sicc. Na₂SO₄) and evaporated under reduced pressure. The oily residue was treated with an equivalent amount of maleic acid in a mixture of EtOH and Et₂O to give crystalline hydrogenmaleate salt which was filtered off and recrystallized.

¹H-NMR (400 MHz, D₂O) δ (ppm): 1.41 (3H, t, J=7.2 Hz, Ch₃), 3.14 (1H, dd, J=16.2, 8.3 Hz, CHCH₂), 3.47 (3H, om, CHCH₂, NCH₂), 4.04 (1H, m, NCH), 5.46 (1H, d, J=6.4, OCH), 6.29 (2H, s, CHCOOH) 7.30–7.45 (4H, om, C₆H₄).

EXAMPLE 3
(1R*,2R*)-2-(1-Ethylhydrazino)-1-indanol hydrogenmaleate (2)

To a solution of 1-oxa-2-azaspiro[2.5]octane (1.12 g. 9.9 mmol) in ether (20 ml) a solution of (1R*,2R*)-2-ethylamino-1-indanol (1.75 g, 9.9 mmol) in THF (25 ml) was added. The reaction mixture was stirred at room temperature for 45 minutes then evaporated to dryness. 5% Hydrochloric acid (50 ml) was added to the residue and the mixture was stirred at ambient temperature for 1 h. The mixture was washed with Et₂O (2×30 ml), made alkaline with Na₂CO₃ under ice-cooling and extracted with EtOAc (3×50 ml). The combined EtOAc extracts were dried (sicc. Na₂SO₄) and evaporated under reduced pressure. The oily residue was treated with an equivalent amount of maleic acid in a mixture of EtOH and Et₂O to give crystalline hydrogenmaleate salt which was filtered off and recrystallized.

¹H-NMR (400 MHz, D₂O): see Example 2

EXAMPLE 4
(1R,*2R*)-2-(1-Methylhydrazino)-1-indanol hydrogenmaleate (4)

To an ice-cooled and stirred suspension of zinc dust (2.62 g, 40 mmol) in H₂O (10 ml) a solution of (1R*,2R*)-2-methylamino-N-nitroso-1-indanol (1.92 g, 10 mmol prepared from (1R*,2R*)-2-methylamino-1-indanol according to Example 1) in AcOH (18 ml) was added dropwise over a period of 45 min. During the addition, the temperature of the reaction mixture was maintained at 20–25° C. by external cooling. After the addition was completed, the mixture was stirred at 50° C. for 1 h, then filtered by suction, and the zinc residue was washed with a mixture of H₂O (15 ml) and AcOH (5 ml). The combined filtrate and washings were concentrated to ca. 10 ml in vacuo. The iced-cooled solution was made basic with NaOH-solution and extracted with Et₂O (4×50 ml). The combined ethereal extracts were dried (sicc. Na₂SO₄) and evaporated in reduced pressure. The crystalline residue was treated with an equivalent amount of maleic acid in a mixture of EtOH and Et₂O to give crystalline hydrogenmaleate salt which was filtered off and recrystallized.

¹H-NMR (400 MHz, D₂O ) δ (ppm): 3.05 (1H , m, CHCH₂), 3.11 (3H, s, NCH₃), 3.43 (1H, m, CHCH₂), 3.86 (1H, m, NCH), 5.47 (1H, d, J=6.6 Hz, OCH), 6.28 (2H, s, CHCOOH), 7.34 (1H, m, C₆H₄), 7.39 (3H, m, C₆H₄).

EXAMPLE 5
(1R*,2R*)-2-(1-Ethylhydrazino)-1-indanol hydrogenmaleate (2)

To a stirred suspension of (1R*,2R*)-2-ethylamino-N-nitroso-1-indanol (1.94 g, 9.4 mmol, prepared from of (1R*,2R*)-2-ethylamino-1-indanol(1.77 g, 10 mmol) according to Example 2), zinc dust (2.46 g, 37.6 mmol) and H₂O (15 ml), glacial acetic acid (3.00 g, 50 mmol) was added dropwise over a period of 1 h. During the addition, the temperature of the reaction mixture was maintained at 25–30° C. by external cooling. Subsequently the reaction mixture was stirred at 60° C. for 1 h, allowed to cool, and the excess zinc dust filtered by suction and washed with H₂O (15 ml). The combined filtrate and washings were made basic with aqueous NaOH-solution and extracted with CHCl₃ (4×50 ml). The combined organic phases were dried (sicc. Na₂SO₄) and evaporated under reduced pressure. The oily residue was treated with an equivalent amount of maleic acid in a mixture of EtOH and Et₂O to give crystalline hydrogenmaleate salt which was filtered off and recrystallized.

¹H-NMR (400 MHz, D₂O ); see Example 2

EXAMPLE 6
(1R,2R)-2-(1-methylhydrazino)-1-indanol hydrogenmaleate (6)

(1R,2R)-2-(1-methylhydrazino)-1-indanol (1.45 g, 8.1 mmol, prepared from (1R,2R)-2-methylamino-1-indanol (1.63 g, 10 mmol) according to Example 1) was treated with an equivalent amount of maleic acid in a mixture of EtOH and Et₂O to give crystalline hydrogenmaleate salt which was filtered off and recrystallized.

¹H-NMR (400 MHz, D₂O) δ (ppm): same as that of the (1S,2S)-enantiomer in Example 1.

EXAMPLE 7

(1S,2S)-2-(1-methylhydrazino)-1-indanol fumarate (7)

(1S,2S)-2-(1-methylhydrazino)-1-indanol (1.43 g, 8 mmol, prepared from (1S,2S)-2-methylamino-1-indanol according to Example 1) was treated with fumaric acid (0.47 g, 4 mmol) in a mixture of EtOH and $Et_2O$ to give crystalline fumarate salt which was filtered off and recrystallized.

$^1$H-NMR (400 MHz, $D_2O$) δ (ppm): 3.05 (2×4H, om, $CHCH_2$, $NCH_3$), 3.42 (2×1H, m, $CHCH_2$), 3.83 (2×1H, m, NCH), 5.46 (2×1H, d, J=6.6 Hz, OCH), 6.50 (2H, s, HOOCCH=CHCOOH), 7.34 (2×1H, m, $C_6H_4$), 7.40 (2×3H, m, $C_6H_4$).

EXAMPLE 8

(1R,2R)-2-(1-methylhydrazino)-1-indanol fumarate (8)

(1R,2R)-2-(1-methylhydrazino)-1-indanol (1.43 g, 8 mmol, prepared from (1R,2R)-2-methylamino-1-indanol according to Example 1) was treated with fumaric acid (0.47 g, 4 mmol) in a mixture of EtOH and $Et_2O$ to give crystalline fumarate salt which was filtered off and recrystallized.

$^1$H-NMR (400 MHz, $D_2O$) δ (ppm): same as that of the (1S,2S)-enantiomer in Example 7.

EXAMPLE 9

(1S,2S)-2-(1-methylhydrazino)-1-indanol succinate (9)

(1S,2S)-2-(1-methylhydrazino)-1-indanol (1.43 g, 8 mmol, prepared from (1S,2S)-2-methylamino-1-indanol according to Example 1) was treated with succinic acid (0.48 g, 4 mmol) in a mixture of EtOH and $Et_2O$ to give crystalline succinate salt which was filtered off and recrystallized.

$^1$H-NMR (400 MHz, $D_2O$) δ (ppm): 2.45 (4H, s, $HOOCCH_2CH_2COOH$), 3.04 (2×4H, om, $CHCH_2$, $NCH_3$), 3.39 (2×1H, m, $CHCH_2$), 3.73 (2×1H, m, NCH), 5.43 (2×1H, d, J=6.5 Hz, OCH), 7.30–7.45 (2×4H, om, $C_6H_4$).

EXAMPLE 10

(1R,2R)-2-(1-methylhydrazino)-1-indanol succinate (10)

(1R,2R)-2-(1-methylhydrazino)1-indanol (1.43 g, 8 mmol, prepared from (1R,2R)-2-methylamino-1indanol according to Example 1) was treated with succinic acid (0.48 g, 4 mmol) in a mixture of EtOH and $Et_2O$ to give crystalline succinate salt which was filtered off and recrystallized.

$^1$H-NMR (400 MHz, $D_2O$) δ (ppm): same as that of the (1S,2S)-enantiomer In Example 9.

EXAMPLE 11

(1S,2S)-2-(1-methylhydrazino)-1-indanol (S,S)-tartrate (11)

(1S,2S)-2-(1-methylhydrazino)-1-indanol (1.43 g, 8 mmol, prepared from (1S,2S)-2-methylamino-1-indanol according to Example 1) was treated with (S,S)-tartaric acid (0.60 g, 4 mmol) in EtOH to give crystalline (S,S)-tartrate salt which was filtered off and recrystallized.

$^1$H-NMR (400 MHz, $D_2O$) δ (ppm): 3.06 (2×4H, om, $CHCH_2$, $NCH_3$), 3.42 (2×1H, m, $CHCH_2$), 3.84 (2×1H, m, NCH), 4.34 (2H, s, HOOCCHOHCHOHCOOH), 5.47 (2×1H, d, J=6.5 Hz, OCH), 7.30–7.45 (2×4H, om, $C_6H_4$).

EXAMPLE 12

(1R,2R)-2-(1-methylhydrazino)-1-indanol (S,S)-tartrate (12)

(1R,2R)-2-(1-methylhydrazino)-1-indanol (1.43 g, 8 mmol, prepared from (1R,2R)-2-methylamino-1-indanol according to Example 1) was treated with (S,S)-tartaric acid (0.60 g, 4 mmol) in a mixture of EtOH and EtOAc to give crystalline (S,S)-tartrate salt which was filtered off and recrystallized.

$^1$H-NMR (400 MHz, $D_2O$) δ (ppm): 3.06 (2×4H, om, $CHCH_2$, $NCH_3$), 3.43 (2×1H, m, $CHCH_2$), 3.84 (2×1H, m, NCH), 4.34 (2H, s, HOOCCHOHCHOHCOOH), 5.47 (2×1H, d, J=6.5 Hz OCH), 7.30–7.45 (2×4H, om, $C_6H_4$).

EXAMPLE 13

(1S,2S)2-(1-methylhydrazino)-1-indanol (R,R)-tartrate (13)

(1R,2R)-2-(1-methylhydrazino)-1-indanol (1.43 g, 8 mmol, prepared from (1R,2R)-2-methylamino-1-indanol according to Example 1) was treated with (R,R)-tartaric acid (0.60 g, 4 mmol) in a mixture of EtOH and EtOAc to give crystalline (R,R)-tartrate salt which was filtered off and recrystallized.

$^1$H-NMR (400 MHz, $D_2O$) δ (ppm): same as that of (1R,2R)-2-(1-methylhydrazino)-1-indanol (S,S)-tartrate in Example 12.

EXAMPLE 14

(1R,2R)-2-(1-methylhydrazino)-1-indanol (R,R)-tartrate (14)

(1S,2S)-2-(1-methylhydrazino)-1-indanol (1.43 g, 8 mmol, prepared from (1S,2S)-2-methylamino-1-indanol according to Example 1) was treated with (R,R)-tartaric acid (0.60 g, 4 mmol) in EtOH to give crystalline (R,R)-tartrate salt which was filtered off and recrystallized.

$^1$H-NMR (400 MHz, $D_2O$) δ (ppm): same as that of (1S,2S)-2-(1-methylhydrazino)-1-indanol (S,S)-tartrate in Example 11.

EXAMPLE 19

(1S,2S)-2-(1-methylhydrazino)-1-methoxyindane Hydrogenmaleate (19)

55% Sodium hydride suspension (2.00 g, 45.9 mmol) was washed with n-hexane and suspended in THF (50 ml). A solution of (1S,2S )-2-methylamino-N-nitroso-1indanol prepared according to Example 1 (2.88 g, 15 mmol) in THF (90 ml) was degassed with $N_2$ flushing and added dropwise to the NaH suspension with stirring and continuous $N_2$ flushing at 0° C. over a period of 1 h. Stirring was continued at 0° C. for 2 h, then a solution of MeI (3.40 g, 24.0 mmol) in THF (30 ml) was added dropwise to the stirred suspension at 0° C. The mixture was allowed to warm to room temperature and the excess of NaH decomposed by addition of MeOH. The solution evaporated to dryness, the residue was dissolved in $H_2O$ (50 ml) and extracted with $Et_2O$ (3×50 ml). The combined ethereal extracts were washed with $H_2O$ (50 ml) then dried ($Na_2SO_4$) and evaporated under reduced pressure to give 2.6 g thick yellow oil which was used in the next step without further purification.

A solution of (1S,2S)-2-methylamino-N-nitroso-1-methoxyindane (2.47 g, 12.0 mmol) in THF (30 ml) was added dropwise to a strirred and ice-cooled suspension of $LiAlH_4$ (1.80 g, 47.4 mmol) in THF (90 ml). The mixture was stirred at 0° C. for 3 h, then allowed to warm to room temperature. The excess of $LiAlH_4$ was decomposed with a mixture of $H_2O$ (3.6 ml) and THF (25 ml), the resulting precipitate was filtered off and washed with EtOAc (2×75 ml). The combined filtratee were dried (sicc. $Na_2SO_4$) and evaporated under reduced pressure. The residue was treated with an equivalent amount of maleic acid in a mixture of EtOH and $Et_2O$ to give crystalline hydrogenmaleate salt, which was filtered off and recrystallized.

$^1$H-NMR (400 MHz, $D_2O$) δ (ppm): 3.01 (3H, s, $NCH_3$), 3.14 (1H, dd, J=5.8, 17.1 Hz, $CHCH_2$), 3.48 (1H, dd, J=8.3, 17.1 Hz, $CHCH_2$), 3.55 (3H, s, $OCH_3$), 4.11 (1H, m, NCH), 5.33 (1H, d, J=4.5 Hz, OCH), 6.29 (2H, s, CHCOOH), 7.36–7.52 (4H, m, $C_6H_4$).

TABLE 1

Physical data of the synthesized racemic compounds

| Number | Structure | M.p. (°C.) | Yield (%) | Formula (M.w.) | Elemental analysis Calcd./Found (%) C | H | N | Synthetic method |
|---|---|---|---|---|---|---|---|---|
| 4 |  | 102–103 | 74<br>62 | $C_{14}H_{18}N_2O_5$<br>(294.30) | 57.14<br>56.89 | 6.16<br>6.01 | 9.52<br>9.43 | Example 4 |
| 2 | | 92–94 | 68<br>45<br>61 | $C_{15}H_{20}N_2O_5$<br>(308.33) | 58.43<br>58.22 | 6.45<br>6.15 | 9.09<br>9.16 | Example 2<br>Example 3<br>Example 5 |

TABLE 2

Physical data of the synthesized enantiomeric compounds

| Number | Structure | M.p. (°C.) | $[\alpha]_D^{20}$ | Yield (%) | Formula (M.w.) | Elemental analysis Calcd./Found (%) C | H | N | Synthetic method |
|---|---|---|---|---|---|---|---|---|---|
| 1 |  | 104–106 | +23<br>(MeOH,<br>c = 0.5) | 74 | $C_{14}H_{18}N_2O_5$<br>(294.30) | 57.14<br>57.37 | 6.16<br>6.03 | 9.52<br>9.45 | Example 1 |
| 6 | | 104–106 | −23<br>(MeOH,<br>c = 0.5) | 72 | $C_{14}H_{18}N_2O_5$<br>(294.30) | 57.14<br>56.86 | 6.16<br>5.92 | 9.52<br>9.49 | Example 6 |
| 7 | | 163–166 | +25<br>(MeOH,<br>c = 0.5) | 72 | $C_{24}H_{32}N_4O_6$<br>(472.54) | 61.00<br>59.61 | 6.83<br>6.70 | 11.86<br>11.84 | Example 7 |
| 8 | | 162–164 | −25<br>(MeOH,<br>c = 0.5) | 69 | $C_{24}H_{32}N_4O_6$<br>(472.54) | 61.00<br>59.99 | 6.83<br>6.76 | 11.86<br>11.72 | Example 8 |

TABLE 2-continued

Physical data of the synthesized enantiomeric compounds

| Number | Structure | M.p. (°C.) | $[\alpha]_D^{20}$ | Yield (%) | Formula (M.w.) | Elemental analysis Calcd./Found (%) C | H | N | Synthetic method |
|---|---|---|---|---|---|---|---|---|---|
| 9 | (structure) | 132–134 | +24 (MeOH, c = 0.5) | 62 | $C_{24}H_{34}N_4O_6$ (474.55) | 60.74 60.53 | 7.22 7.18 | 11.81 11.87 | Example 9 |
| 10 | (structure) | 130–132 | −22 (MeOH, c = 0.5) | 65 | $C_{24}H_{34}N_4O_6$ (474.55) | 60.74 60.81 | 7.22 7.05 | 11.81 11.64 | Example 10 |
| 11 | (structure) | 170–173 | +13 (MeOH, c = 0.5) | 73 | $C_{24}H_{34}N_4O_8$ (506.55) | 56.91 56.68 | 6.77 6.39 | 11.06 11.01 | Example 11 |
| 12 | (structure) | 155–157 | −33 (MeOH, c = 0.5) | 66 | $C_{24}H_{34}N_4O_8$ (506.55) | 56.91 57.14 | 6.77 6.75 | 11.06 10.92 | Example 12 |
| 13 | (structure) | 156–158 | +31 (MeOH, c = 0.5) | 68 | $C_{24}H_{34}N_4O_8$ (506.55) | 56.91 56.60 | 6.77 6.43 | 11.06 10.99 | Example 13 |
| 14 | (structure) | 171–173 | −13 (MeOH, c = 0.5) | 71 | $C_{24}H_{34}N_4O_8$ (506.55) | 56.91 56.86 | 6.77 6.60 | 11.06 10.87 | Example 14 |
| 19 | (structure) | 113–115 | +33 (c = 0.5, MeOH) | | $C_{15}H_{20}N_2O_5$ (308.34) | | | | Example 19 |

EXAMPLE 15

In Vitro Inhibition of VAP-1SSAO Activity

VAP-1 SSAO activity was measured using the coupled colourimetric method essentially as described for monoamine oxidase and related enzymes (Holt, A., et al., *Anal. Biochem.* 244:384–392 (1997)). Recombinant human VAP-1 SSAO expressed in Chinese Hamster Ovary (CHO) cells was used as a source of VAP-1 SSAO for activity measurements. Native CHO cells have negligible SSAO activity. These cells and their culture have previously been described (Smith, D. J., et al., *J. Exp. Med.* 188:17–27 (1998)). A cell lysate was prepared by suspending approximately $3.6 \times 10^8$ cells in 25 ml lysis buffer (150 mM NaCl, 10 mM Tris-Base pH 7.2, 1.5 mM $MgCl_2$, 1% NP40) and incubating at 4° C. overnight on a rotating table. The lysate was clarified by centrifugation at 18000 g for 5 min at room temperature and the supernatant used directly in the assay. The VAP1 SSAO assay was performed in 96 well microtitre plates as follows. To each well was added a predetermined amount of inhibitor if required. The amount of inhibitor varied in each assay but was generally at a final concentration of between 1 nM and 50 µM. Controls lacked inhibitor. The inhibitor was in total volume of 20:1 in water. The following reagents were then added. 0.2M potassium phosphate buffer pH 7.6 to a total reaction volume of 200 µl, 45 µl of freshly made chromogenic solution containing 1 mM 2,4-dichlorophenol, 500 µM 4-aminoantipyrine and 4 U/ml horseradish peroxidase and an amount of CHO cell lysate containing VAP-1 SSAO that caused a change of 0.6 $A_{490}$ per h. This was within the linear response range of the assay. The plates were incubated for 30 min at 37° C. and the background absorbance measured at 490 nm using a Wallac Victor II multilabel counter. To initiate the enzyme reaction 20 µl 10 mM benzylamine (final concentration=1 mM) was added and the plate incubated for 1 h at 37° C. The increase in absorbance, reflecting VAP-1 SSAO activity, was measured at 490 nm. Inhibition was presented as percent inhibition compared to control after correcting for background absorbance and $IC_{50}$ values calculated using GraphPad Prism.

EXAMPLE 16

Comparison of VAP1 SSAO Activity Versus Total Rat MAO Activity

Rat MAO was prepared from rat liver by rinsing the 1 g liver sample several times in 14 ml KCl-EDTA-solution to remove all blood. Then 1 g liver sample was homogenised in 4 ml ice-cold potassium phosphate buffer (0.1 M, pH 7.4) with an Ultra-Turrax homogeniser (setting 11,000 rpm, 4×10 s). After centrifugation at 500 g for 10 min at 4° C. the supernatant was carefully withdrawn and was centrifuged at 12,300 g for 15 min at 4° C. The supernatant was discharged and sedimented mitochondria were resuspended in 4 ml fresh phosphate buffer and centrifuged as previously. The mitochondria were suspended in 4 ml phosphate buffer and homogenized with an Ultra-Turrax homogeniser (setting 11,000 rpm, 2×10 s). Mitochondrial preparate was aliquoted and stored at -70° C. Total MAO activity was measured in a similar way as for VAP1 SSAO except that 2,4-dichlorophenol was replaced by 1 mM vanllic acid. To each well was added a predetermined amount of Inhibitor if required. The amount of inhibitor varied in each assay but was generally at a final concentration of between 10 nM and 800 µM. Controls lacked inhibitor. The inhibitor was in a total volume of 20:1 in water. The following reagents were then added. 0.2 M potassium phosphate buffer pH 7.6 for a total reaction volume of 300 µl, 50 µl of freshly made chromogenic solution (as above) and 50 µl of MAO preparation. The plates were incubated for 30 min at 37° C. and the background absorbance measured at 490 nm using a Wallac Victor II multilabel counter. To initiate the enzyme reaction 20 µl of 5 mM tyramine (final concentration 0.5 mM) was added and the plate incubated for 1 h at 37° C. The increase in absorbance, reflecting MAO activity, was measured at 490 nm. Inhibition was presented as percent inhibition compared to control after correcting for background absorbance and $IC_{50}$ values calculated using GraphPad Prism. Clorgyline and pargyline (inhibitors of MAO-A and -B respectively) at 0.5 µM were added to some wells as positive controls for MAO inhibition.

The ability of compounds of Examples 1 to 14 to inhibit VAP-1 SSAO activity with specificity for VAP-1 SSAO over rat MAO is shown in Table 3. The results indicate that the compounds of the invention are specific inhibitors of human VAP-1 SSAO activity. The compounds of the present invention are therefore expected to have therapeutic utility in the treatment of diseases and conditions in which the SSAO activity of the human adhesion molecule VAP-1 plays a role.

TABLE 3

Potency and specificity of Examples 1 to 14

| Example Compound | VAP-1 SSAO inhibitory activity $IC_{50}$ uM | Total MAO inhibitory activity $IC_{50}$ uM | Selectivity for VAP-1 SSAO over MAO |
|---|---|---|---|
| 4 | 0.66 | 21 | 32 |
| 2 | 5.30 | 19 | 4 |
| 1 | 0.70 | 22 | 31 |
| 6 | 0.65 | 19 | 29 |
| 7 | 0.47 | 13 | 28 |
| 8 | 0.56 | 12 | 21 |
| 9 | 0.62 | 16 | 26 |
| 10 | 0.66 | 15 | 23 |
| 12 | 0.66 | 20 | 30 |
| 14 | 0.71 | 20 | 28 |
| 11 | 0.71 | 22 | 31 |
| 13 | 0.66 | 19 | 29 |
| 19 | 4.32 | 14 | 3 |

EXAMPLE 17

Inhibition of Carrageenan-evoked Rat Paw Oedema
The Model in the Literature:
Carrageenan-induced rat paw oedema has been extensively used in the evaluation of anti-inflammatory effects of various compounds and it is useful in assessing the efficacy of compounds to alleviate acute inflammation (Whiteley P E and Dalrymple S A (1998) Models of inflammation: carrgeenan-induced paw edema in the rat, in Current Protocols in Pharmacology (Enna S J, Williams M, Ferkany J W, Kenakin T, Porsolt R E and Sullivan J P eds) pp 5.4.1–5.4.3, John Wiley & Sons, New York.). The oedema is biphasic (Vinegar el al., *J. Pharmacol. Exp. Ther.* 166:96–103 (1969)). The first phase is not readily inhibited by cyclooxygenase inhibitors while the later phase is (Seibert et al., *Proc. Natl Acad. Sc (USA)* 91:12013–12017 (1994)). The full development of the oedema has also been demonstrated to be neutrophil-dependent (Salvemini et al., *Br. J. Pharmacol.* 118:829–838. (1996)).
Description of the Model Used:
Female Sprague Dawley rats were used and compound 4 was injected at 3 different does of 10, 32 and 100 mg $kg^{-1}$ intraperitoneally 15 min prior to carrageenan exposure. Oedema in the paws was induced as previously described (Whiteley P E and Dalrymple S A (1998) Models of inflammation: carrageenan-induced paw edema in the rat, in Current Protocols in Pharmacology (Enna S J, Williams M, Ferkany J W, Kenakin T. Porsolt R E and Sullivan J P eds) pp 5.4.1–5.4.3, John Wiley & Sons, New York.).) by injecting 0.05 ml of a 0.5% solution of carrageenan (Type IV Lambda, Sigma) in saline with a 27-G needle subcutaneously in the right hind foot pad. The size of the tested foot of each animal was measured volumetrically using a plethysmometer (Ugo Basile, Cat, No. 1750) before induction of oedema, and at 60 and 180 min after carrageenan injection. Three hours after injection of carrageenan the animals were killed in a $CO_2$ atmosphere. Both hind-paws were removed by severing them at the tarso-tibial joint and they were weighed immediately using a scale accurate to 0.0001 g.

Figure 1:
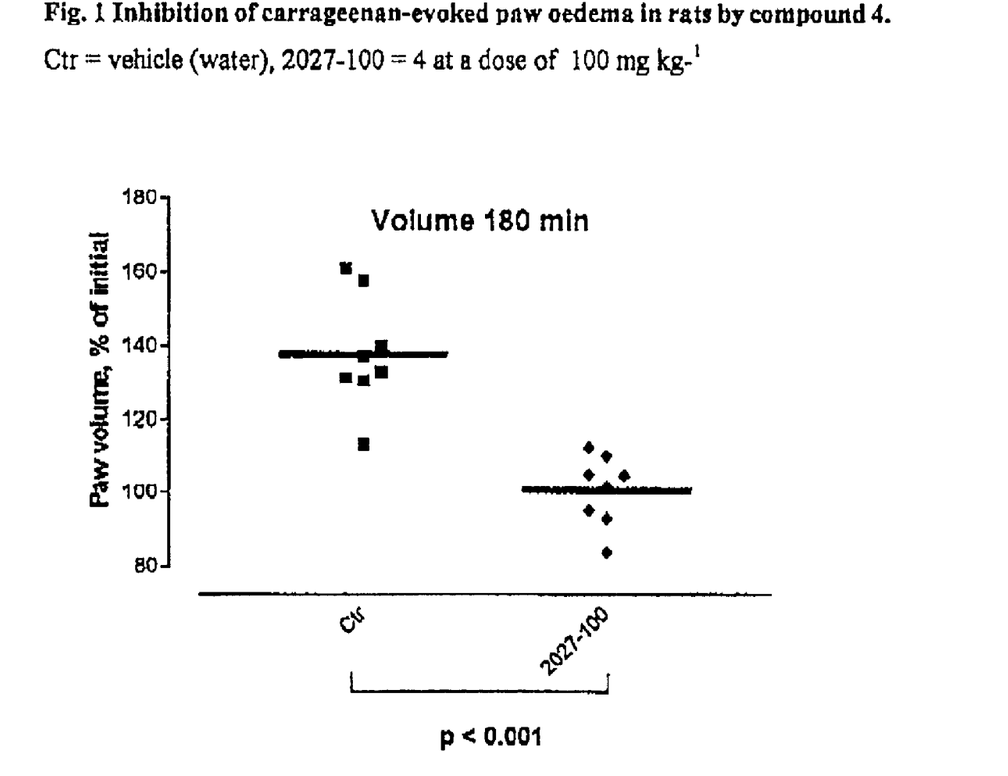
FIG. 1 shows the inhibition of carrageenan-evoked paw oedema in rats by compound 4, as described in Example 17. Ctr=vehicle (water), 2027–100=4 at a dose of 100 mg kg$^{-1}$.

Outcome:

The 100 mg $kg^{-1}$ dose clearly and significantly reduced the paw swelling at 60 min (p<0.05 by Dunnett's test following analysis of variance) and 180 min (FIG. 1) in which the oedema was nearly totally inhibited (p<0.001 by Dunnett's test following analysis of variance),

EXAMPLE 18

Inhibition of Collagen-induced Arthritis in Mouse

The Model in the Literature:

Mouse collagen-induced arthritis (CIA) is a frequently used model both for studying the basic mechanisms of autoimmune arthritis and in assessing the efficacy of potential antiarthritic agents (van den Berg and Joosten, 1999 in In Vivo Models of Inflammation (Morgan D W and Marshall L A eds) pp 51–75, Birkhauser Verlag, Basel). Compounds acting through various mechanisms have been demonstrated to be effective in the model and they include cyclooxygenase inhibitors, interleukins 4 and 10, leukotriene synthesis inhibitors and anti-TNF antibodies (Joosten et al., *J. Immunol.* 159:4094–4102, 1997; van den Berg and Joosten, 1999 in In Vivo Models of Inflammation (Morgan D W and Marshall L A eds) pp 51–75, Birkhauser Verlag, Basel)).

Description of the Model Used:

The study was conducted with groups of 14 mice to obtain statistically valid results. For arthritis induction DBA/1 mice (male, aged 10–12 weeks, approximate weight 25 g) were immunized with bovine type II collagen (100 μg) emulsified in Freund's complete adjuvant by four subcutaneous injections in the back. At day 21, animals were boosted with an i.p. injection of 100 μg collagen type II diluted in PBS. This strain is highly susceptible to CIA induced with bovine type II collagen. After the second immunization, polyarthritis starts to develop in 1 to 2 weeks, with a disease incidence of approx. 80% at day 38 (Joosten et al., *J. Immunol.* 159:4094–4102, 1997). Arthritis development was scored from day 21 onwards. Animals were treated for 2.5 weeks starting after the second booster but before the arthritis onset (day 23). Intraperitoneal medication with compound 4 (10 or 50 mg $kg^{-1}$ twice daily) was initiated at day 23 and continued until day 37.

Figure 2:
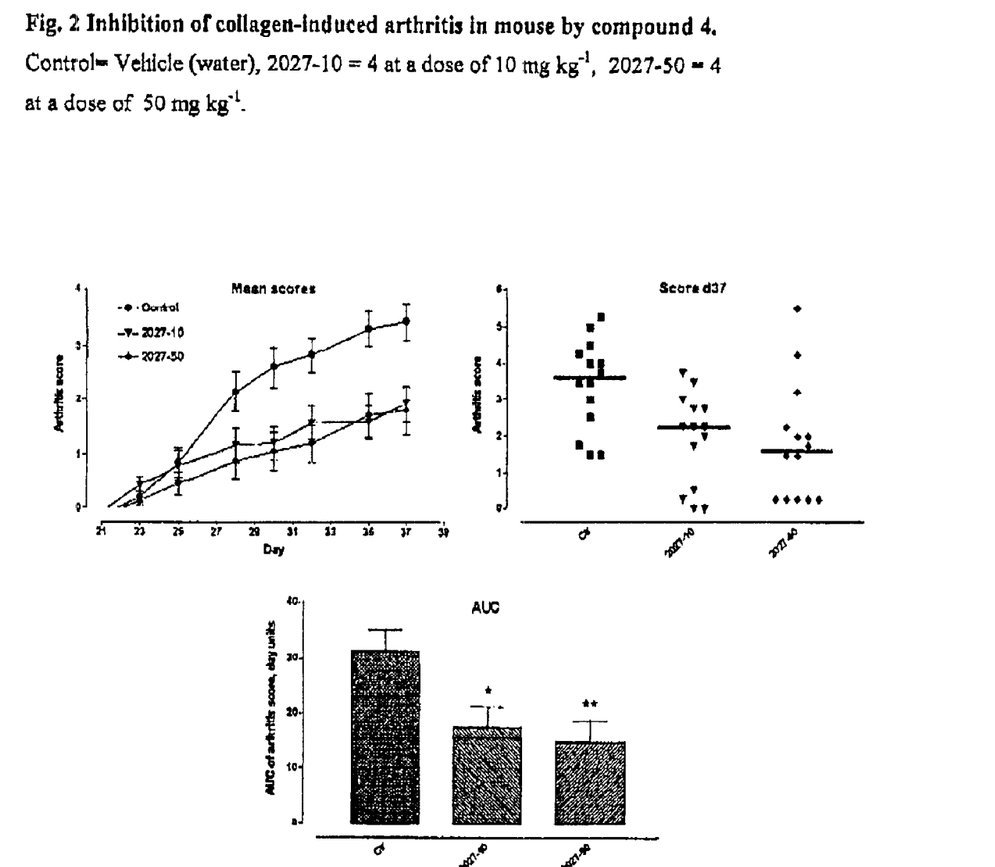
FIG. 2 shows the inhibition of collagen-induced arthritis in mouse by compound 4, as described in Example 18. Control=Vehicle (water); 2027-10=4 at a dose of 10 mg kg$^{-1}$; 2027-50=4 at a dose of 50 mg kg$^{-1}$.

Outcome:

A reduction in the final arthritis score (p<0.05 for either dose by Dunn's test following Kruskal-Wallis test) and cumulative score (p<0.05 for 10 mg $kg^{-1}$ and p<0.01 for 50 mg $kg^{-1}$ dose by Dunn's test following Kruskal-Wallis test) was detected (FIG. 2). There was no statistically significant effect on the lag time preceding the first signs of arthritis.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula I:

I or an isomer or a pharmaceutically acceptable solvate, hydrate, or salt thereof;

wherein:

$R^1$ is hydrogen or $(C_1-C_4)$alkyl, aralkyl, $(C_2-C_5)$ alkanoyl, aroyl or heteroaroyl;

$R^2$ is hydrogen, optionally substituted $(C_1-C_4)$alkyl, or optionally substituted aralkyl;

$R^3-R^5$ and $R^{10}$, which can be the same or different, are hydrogen, optionally substituted $(C_1-C_4)$alkyl, optionally substituted aralkyl, optionally substituted phenyl or optionally substituted heteroaryl;

$R^3$ and $R^{10}$ are cis or trans arranged;

$R^{11}$ is hydrogen, $(C_1-C_4)$alkyl, $(C_2-C_5)$alkanoyl or aralkyl;

$R^6-R^9$, which can be the same or different, are hydrogen, optionally substituted $(C_1-C_4)$alkyl, halogen, hydroxy, optionally substituted $(C_{14}-C_4)$alkoxy, optionally substituted aralkyloxy, or $(C_1-C_4)$alkylamino;

n is 1 or 3, provided that $R^1$ is not methyl when $R^2$ is methyl, n is 1 and $R^3$ to $R^{11}$ are hydrogen.

2. The compound according to claim 1, wherein, in the compound of the Formula I, n has the meaning of 1.

3. The compound according to claim 1, wherein, in the compound of the Formula I, $R^1$ has the meaning of hydrogen.

4. The compound according to claim 1, wherein, in the compound of the Formula I, $R^2$ has the meaning of unsubstituted $(C_1-C_4)$alkyl.

5. The compound according to claim 1, wherein, in the compound of the Formula I, $R^{11}$ is hydrogen.

6. The compound according to claim 1, wherein, in the compound of the Formula I, $R^3$ is hydrogen.

7. The compound according to claim 1, wherein, in the compound of the Formula I, $R^4$, $R^5$ and $R^{10}$ are hydrogen.

8. The compound according to claim 1, wherein, in the compound of the Formula I, $R^6$, $R^7$, $R^8$ and $R^9$ are hydrogen.

9. A pharmaceutical composition comprising a compound of any one of the claims 1 to 8 and a pharmaceutically acceptable carrier and a diluent.

10. A process for preparing a compound of claim 1, comprising:

subjecting an amino alcohol of the Formula II

II to N-nitrosation, to form a compound of the Formula III

III which compound of the formula III is thereafter reduced to give the desired compound of the formula I, in which the substituents $R^1$ to $R^{11}$ and n have the meanings given in claim 1, or an isomer, solvate, hydrate or salt thereof.

11. A process for preparing a compound of the Formula I of claim 1, comprising reacting an amino alcohol of the Formula II

II wherein $R^{11}$ is hydrogen, with an oxaziridine of the Formula V

V wherein $R^{12}$ and $R^{13}$ have the meaning of $C_1$–$C_4$ alkyl groups, or together represent a 5–7-member saturated carbocycle, to give an oxadiazine of the formula IV

IV which is hydrolysed to form the desired hydrazine alcohol of the formula I, wherein $R^{11}$ and $R^1$ are hydrogen, which compound obtained, if desired, is converted to a compound of the Formula I wherein $R^{11}$ and $R^1$ have a meaning other than hydrogen as defined in claim 1, whereby the substituents $R^2$ to $R^{10}$ and n have the meanings given in claim 1, or an isomer, solvate, hydrate or salt thereof.

* * * * *